US007323299B2

(12) United States Patent
Cambareri et al.

(10) Patent No.: US 7,323,299 B2
(45) Date of Patent: Jan. 29, 2008

(54) METHODS FOR IN VIVO DIVERSIFICATION OF SINGLE GENES

(75) Inventors: Edward B. Cambareri, Woodside, CA (US); Eli E. Kato, Irvine, CA (US)

(73) Assignee: Neugenesis Corporation, Burlingame, CA (US)

( * ) Notice: Subject to any disclaimer, the term of this patent is extended or adjusted under 35 U.S.C. 154(b) by 593 days.

(21) Appl. No.: 10/239,288

(22) PCT Filed: Mar. 20, 2001

(86) PCT No.: PCT/US01/09166

§ 371 (c)(1),
(2), (4) Date: Apr. 15, 2003

(87) PCT Pub. No.: WO01/70946

PCT Pub. Date: Sep. 27, 2001

(65) Prior Publication Data

US 2003/0215933 A1 Nov. 20, 2003

Related U.S. Application Data

(60) Provisional application No. 60/190,939, filed on Mar. 21, 2000.

(51) Int. Cl.
| | |
|---|---|
| *C12Q 1/68* | (2006.01) |
| *G01N 33/53* | (2006.01) |
| *G01N 33/569* | (2006.01) |
| *C12N 1/21* | (2006.01) |
| *C07H 21/02* | (2006.01) |
| *C12N 15/63* | (2006.01) |

(52) U.S. Cl. .................. 435/6; 435/7.2; 435/7.31; 435/252.3; 536/23.1

(58) Field of Classification Search .............. None
See application file for complete search history.

(56) References Cited

U.S. PATENT DOCUMENTS 6,372,497 B1 * 4/2002 Stemmer ................ 435/440

FOREIGN PATENT DOCUMENTS

WO WO 99/27072 6/1999

OTHER PUBLICATIONS

Singer et al., DNA Methylation Associated with Repeat-Induced-Point Mutation in *Neurospora crassa*, 1995, Mol. Cell. Biol. 15: 5586,5594.*
Cambareri et al., Science (1989) 244(4912):1571-1575.
Cambareri et al., Genetics (1991) 127(4):699-710.
Fincham, Curr Genet (1990) 18:441-445.
Hamann et al., Mol. Gen. Genet. (2000) 263(6):1061-1069.
Harris et al., Genetics (1993) 135(1):5-16.
Irelan et al., Genetics (1994) 138:1093-1103.
Selker et al., Cell (1987) 51:741-752.
Selker et al., Fungal Genetics Newsletter (1989) 36:73-76.
Singer et al., Fungal Genetics Newsletter (1995a) 42:74075.
Barbato C., et al. (1996) *Molecular & General Genetics* 252(4):353-361.
Foss E.J., et al. (1991) *Genetics* 127(4):711-717.

* cited by examiner

*Primary Examiner*—David Guzo
*Assistant Examiner*—Michele K. Joike
(74) *Attorney, Agent, or Firm*—Morrison & Foerster LLP

(57) ABSTRACT

Methods and compositions are provided for the efficient in vivo diversification of gene-products in filamentous fungi, starting from (but not limited to) two or more copies of a single gene constituent. The diversification involve use of the Repeat-Induced Point mutation (RIP) process in *N. crassa*, and other fungi that have analogous mutational processes. The invention takes advantage of the induction of G:C to A:T transition mutations specific to duplicated DNA sequences during the premeiotic dikaryon phase of the life cycle of the fungus. The methods and compositions of the invention can be utilized to generate diversity in target genes, and are proposed for the purpose of altering and generating novel forms and activities of gene-products thus encoded. Duplicated genes may be introduced into the organism and are present either in tandem, or at separate ectopic locations within the genome of the fungus. After crossing the resulting transformant(s), sexual progeny can then be selected which contain the mutated gene, and subsequently screened for a desired product.

6 Claims, 3 Drawing Sheets

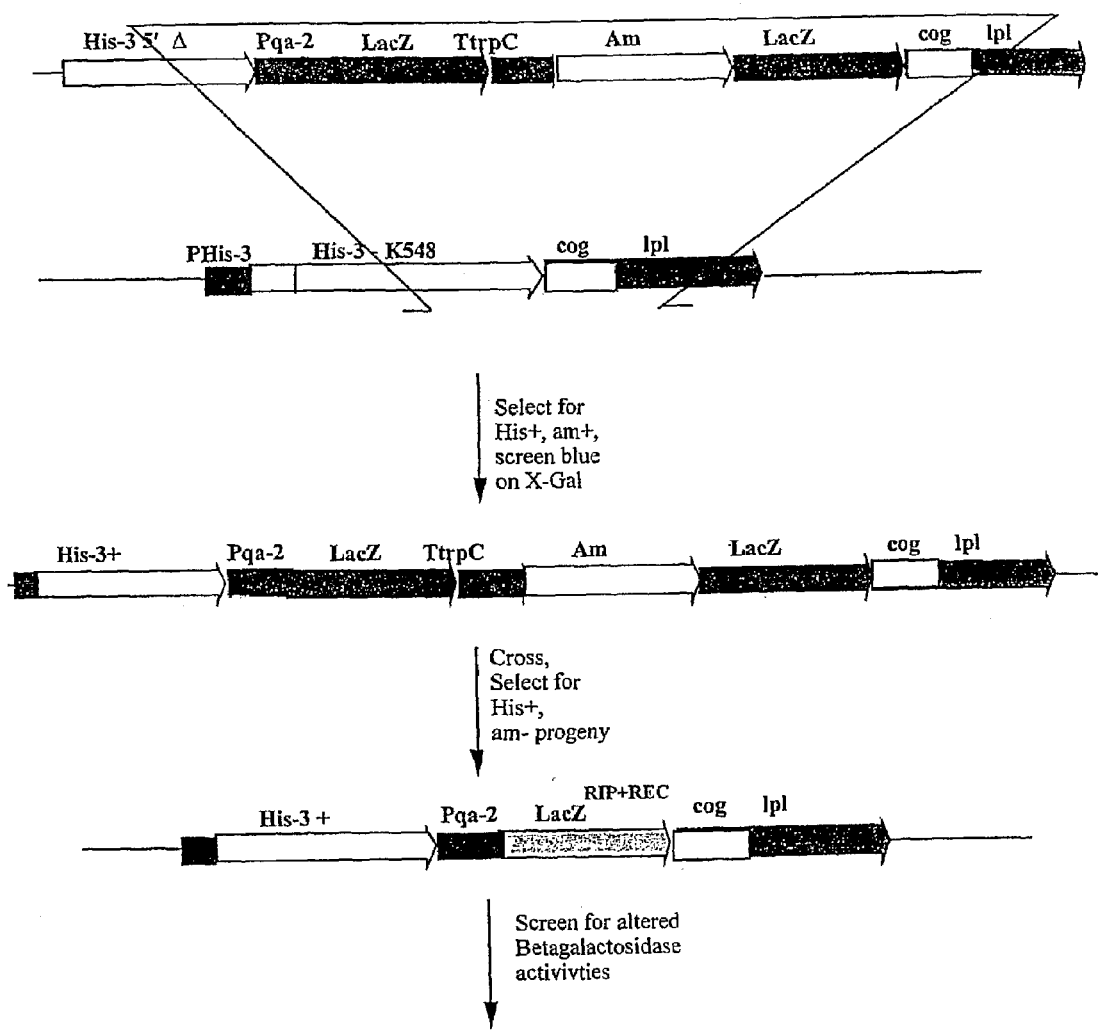

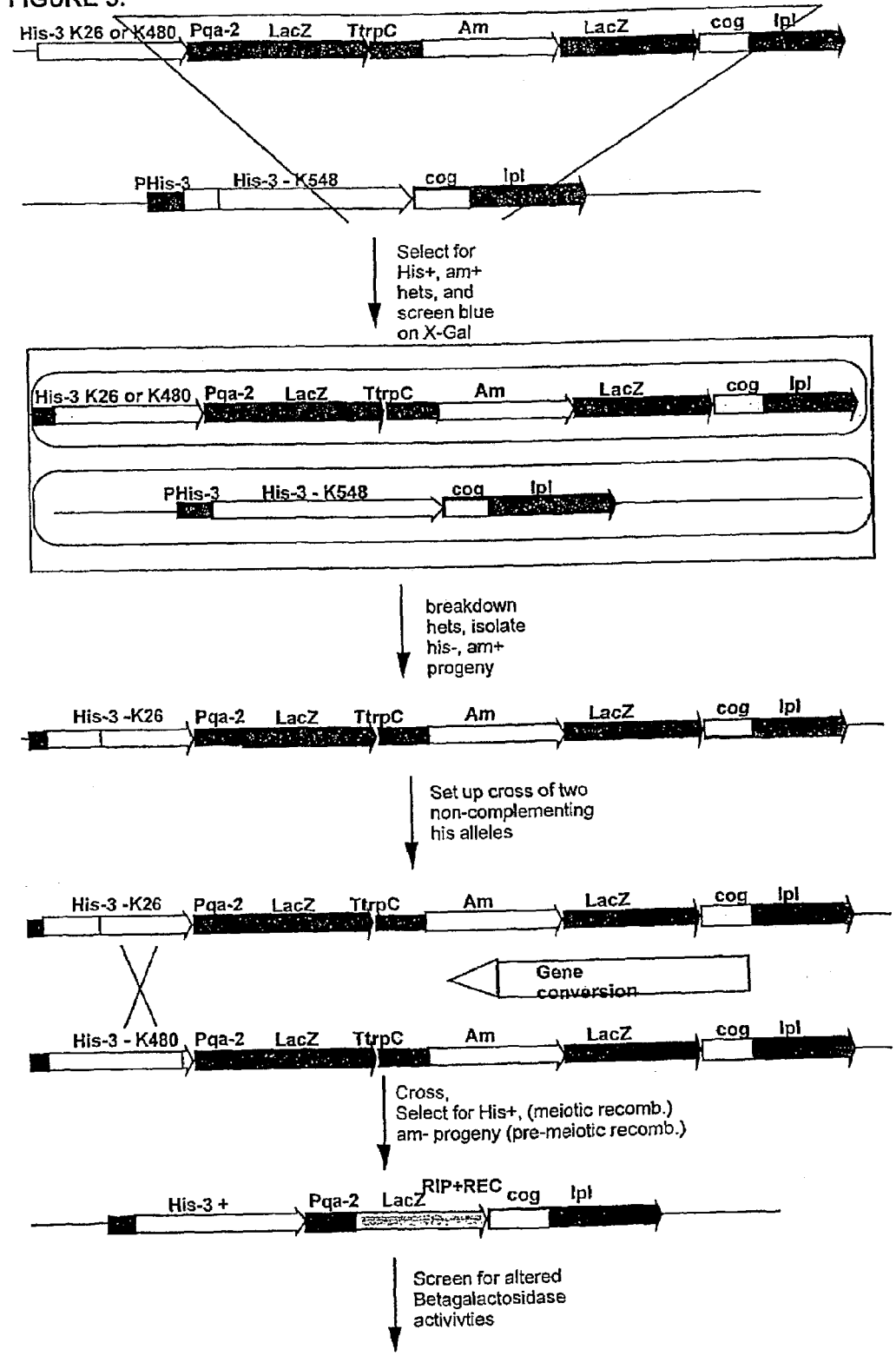

METHODS FOR IN VIVO DIVERSIFICATION OF SINGLE GENES

This application is a National Phase application of PCT/US01/09166, filed Mar. 21, 2001, which claims benefit of priority from U.S. Provisional Patent Application No. 60/190,939, filed on Mar. 21, 2000.

FIELD OF THE INVENTION

The present invention relates to the field of directed evolution nucleic acids, or gene shuffling, and discloses novel methods and compositions for introducing diversity into polynucleotide and polypeptide sequences. The present invention allows generation of new sequences that have desirable properties, by virtue of very high frequency mutation and recombination events in vivo (within a living cell) between two (or more) identical copies of a single polynucleotide sequence in a specialized dikaryotic cell during the premeiotic stage of the lifecycle of the cell. Cells capable of displaying these very high frequency events include those of *Neurospora crassa* and similar fungi. The occurrence of mutation, followed by recombination, of a polynucleotide sequence duplicated at least once in such cells results in the production of a large population of new sequence variants. Appropriate in vivo or in vitro selection and/or screening for such sequence variants permits identification and isolation of new forms of the polynucleotide sequence as well as its products and metabolites resulting from its expression.

BACKGROUND ART

Directed evolution is the introduction and identification of new sequence differences in genes and gene products to expand their usefulness. The use of procedures to introduce heterology and to recombine and reassort DNA gene sequences for the purpose of producing novel forms and activities of the products of those genes has taken several forms, each with its advantages and disadvantages. Several in vitro (test-tube) methods have been described, including those that use insertion of randomized oligonucleotides into genes (Suzuki, Baskin, Hood, & Loeb, 1996), artificial exon shuffling of natural variants of genes by recombinant DNA methods, random mutagenesis by error-prone PCR (Cadwell & Joyce, 1993), and sexual PCR methods (Crameri, Bermudez, Raillard, & Stemmer, 1998; Stemmer, 1994; Zhang, Dawes, & Stemmer, 1997), as disclosed in Stemmer et al. in U.S. Pat. No. 5,811,238, issued Sep. 22, 1998, and Minshull et al., U.S. Pat. No. 5,837,458, issued Nov. 17, 1998.

All of the above methods of in vitro-manipulated sequences have the drawback that they require subsequent introduction of the altered sequences into a test cell for subsequent protocols, such as selection and/or screening. Since large populations of newly altered sequences are required in order to find the rare instances of beneficially altered properties, large numbers of transformations are necessary to introduce each altered sequence into a cell where the effects of the alterations can be gauged. This difficulty is frequently compounded in cases where multiple rounds of mutagenesis and reassembly, and subsequent retransformation, are used.

In vivo diversification of genes using homologous meiotic recombination of heterologous genes, as disclosed in Catcheside et. al. in U.S. patent application Ser. No. 08/977,171 (Reagents and Methods for Diversification of DNA, filed November, 1997), greatly reduces the number of transformations of DNA molecules into cells that are required. This method, however, requires initial sequence differences between the two genes that are the partners in the recombination event in order to achieve new combinations of sequence. This limits the method to diversification of genes that have existing nucleotide differences, such as between natural gene variants found in related species, or molecules that have been diversified by one of the aforementioned in vitro methods. Also, the homologous recombination machinery that recombines the two subject genes is limited to sequences with relatively high levels of sequence identity. Generally, recombination is limited to the range of 1-5% heterology (Harris, Rudnicki, & Haber, 1993). Most critically, single polynucleotide sequences without close homologues cannot be diversified by this method.

The present invention advances the previous work by providing an effective means to diversify polynucleotide sequences in vivo without the need for large numbers of transformation steps. The methods and compositions of the invention are useful in the production of new gene products, metabolites, and phenotypes as well as providing information on the structure/function relationship of the products encoded by a polynucleotide sequence.

SUMMARY OF THE INVENTION

The present invention permits the in vivo diversification of a single polynucleotide sequence from any source to generate new and useful variants that can be directly selected and/or screened for without the need for large numbers of transformations. Large and diverse populations of new polynucleotide molecules can be generated and segregated into individual clones. Every C or G nucleotide within a target polynucleotide sequence is a potential target for transitional mutation, and resultant polynucleotide molecules containing single or multiple point mutations can be generated in the same population with a single cross.

The present invention can also function synergistically with the meiotic recombination method for generation of diversity described in U.S. patent application Ser. No. 08/977,171 (Reagents and Methods for Diversification of DNA, filed November, 1997 now U.S. Pat. No. 6,232,112), which is hereby incorporated by reference as if fully set forth. Premeiotic mutation and recombination can generate a large pool of diversified polynucleotide sequences, which subsequently can be acted upon by the meiotic recombination machinery in the same cell. The combination of these cellular events can result in an exponential increase in the diversity present amongst progeny cells produced from a single cross with two or more identical copies of a single gene.

Thus the present invention provides methods and compositions for the in vivo diversification of polynucleotide sequences. Methods of the invention comprise the introduction of more than one copy of a target polynucleotide sequence into a cell capable of undergoing premeiotic mutation and recombination to result in the diversification of the duplicated sequences. The cells for diversifying target polynucleotide sequences of the present invention are generated by introducing two or more copies of a target polynucleotide sequence into a cell capable of sexual fusion with any strain of the opposite mating type. Sexual fusion induces the sexual cycle and the concomitant premeiotic mutation and recombination.

In addition to providing an in vivo method of generating diversity in a target sequence, these cells may be selected or screened for the production of useful gene products or metabolites as well as the presence of useful phenotypes, such as catabolism of particular compounds or altered viability under specialized conditions. Aside from standard selection and screening methods, the cells can also contain a reporter construct or selection marker sensitive to the expression of a particular gene product or to the production of a particular metabolite or catabolic breakdown product. Alternatively, the cells can be screened with a reporter molecule sensitive to the presence of a particular metabolite or catabolic activity. Moreover, and in addition to identification based on metabolic activity, the cells can be screened and/or selected for altered viability under various growth and environmental conditions, such as but not limited to temperature, nutrient source, pH, humidity, oxygen concentration, light, physical (like UV) or chemical mutagens, toxic agents, and osmolarity/salinity, conferred by expression or presence of the diversified sequences.

The identified cells are useful based on their metabolic activity to either i) be producers of desirable gene products and/or metabolites or ii) to show altered phenotype(s) indicative of the presence of the diversified gene or gene-product. Moreover, a cell can be used to isolate and clone novel diversified nucleic acid sequences conferring desirable activities. Examples of such activities include, but are not limited to, those involved in cellular regulatory, structural, enzymatic, metabolic, and catabolic activities.

Thus the invention relates to the diversification of polynucleotide sequences from any source, including animals, plants, microorganisms, and viruses. In addition to being from a known source, the sequence may also be from an unknown organism or a mixture of known and/or unknown organisms found in nature. Additionally, the invention includes the use of polynucleotide sequences previously subjected to intentional modification or mutagenesis, such as substitutions, insertions and deletions, prior to their introduction as more than one copy into a cell for diversification. Any combination of polynucleotide sequences, whether from known or unknown, characterized or uncharacterized, synthetic or naturally occurring, or previously altered or naturally occurring, may be used in the diversification methods of the invention.

Additionally, the invention provides a means of studying the structure to function relationship of a target polynucleotide sequence by observing the sequence positions that are diversified, as well as the nature of the diversification. By comparing a given target sequence before and after diversification in combination with the various gains or losses in functionality, information on the relationship between various structures encoded by the sequence and the functionality imparted by the structure can be elucidated. With such information, additional polynucleotide sequences can be designed with alterations or combinations of alterations not found after in vivo diversification.

BRIEF DESCRIPTION OF THE FIGURES

FIG. 2 shows a schematic representation of the RIP mediated diversification process.

FIG. 3 shows a schematic representation of an optional embodiment of the invention for RIP mediated diversification.

DETAILED DESCRIPTION OF THE PREFERRED EMBODIMENTS

Figure 1:
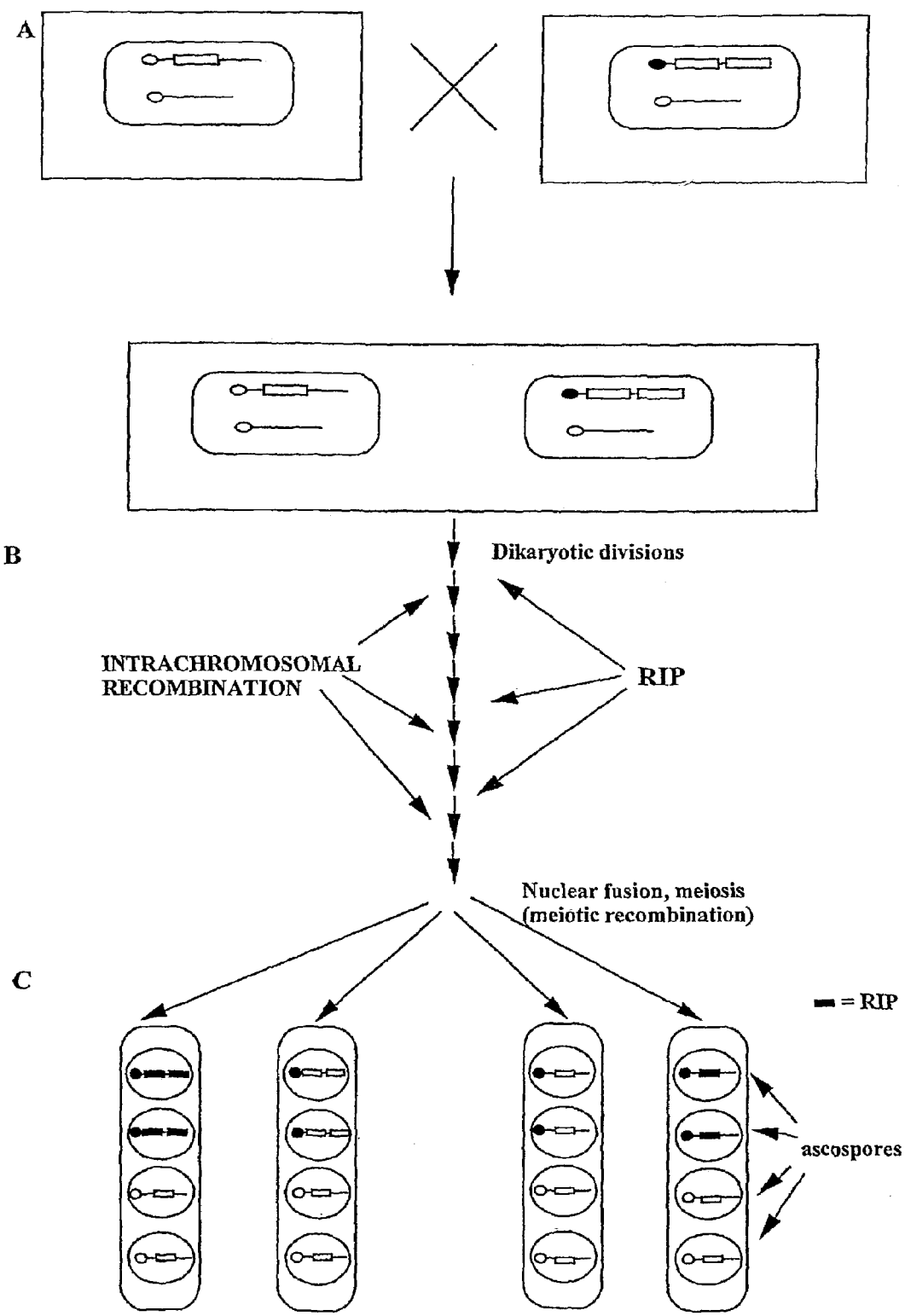
FIG. 1 shows a schematic of the RIP mutation process. Panel A shows a cross between two haploid cells, one of which contains a duplicated sequence, to form a single cell. Panel B indicates the particular dikaryon stage of the sexual cycle during which RIP mutation may occur or not occur at any given cell division. Panel C shows the results of two meiotic and one mitotic event to yield 8 ascospores.

One cellular process that can induce mutations is known as Repeat Induced Point (RIP) mutation, a phenomenon discovered in *Neurospora crassa*, whereby duplicated sequences are subjected to mutation during the sexual cycle, but prior to meiosis (Selker, Cambareri, Jensen, & Haack, 1987). RIP has also been found to occur in *Podospora anserina* (Hamann, Feller, Osiewacz, 2000). RIP mutation is presently used to inactivate specific DNA sequences in order to obtain null alleles of the gene of interest (Selker, Cambareri, Garrett, Jensen, Haack, Foss, et al., 1989). Such alleles are easily isolated due to the high efficiency of RIP mutation, and the multiple mutations typically induced in the target gene sequences (Cambareri, Jensen, Schabtach, & Selker, 1989), and the heavy cytosine DNA-methylation that is frequently associated with RIP mutations.

The present invention, however, utilizes an unobvious aspect of certain types of RIP mutation events. Rather than using RIP to inactivate gene sequences, the invention utilizes RIP as a tool to induce mutations to increase the functional diversity of polynucleotide sequences, including exogenous sequences introduced into an RIP capable cell. Diversification of product encoding sequences that are sparsely altered, which avoids situations where DNA methylation occurs, followed by appropriate selection and/or screening permits the generation of gene products with altered activity, specificity or stability.

The specificity of RIP mutation allows mutagenesis of an entire sequence or the targeted mutagenesis of specific portions of a sequence. Only duplicated sequences in the same haploid nucleus are subject to the process, and only during a particular stage of the sexual cycle (see FIG. 1, panel B). RIP mutation occurs in the 7-10 cell divisions within the dikaryon stage of the N. crassa lifecycle, and may occur or not occur at any given division. Overall, tandemly linked duplicated DNA is found in progeny to have been RIP mutated at a frequency of roughly 95%.

However, the duplicated sequences can frequently 'loop out' or undergo intrachromosomal recombination at a similarly high frequency. When this occurs, the effective target (the duplicated gene) for RIP mutation is lost, and the resulting single copy of the gene sequence is no longer a substrate for the mutational process. This premeiotic intrachromatid recombination, while temporally coincident with RIP mutation, does not appear to be mechanistically related to the latter process (Cambareri, Singer, & Selker, 1991; Irelan, Hagemann, & Selker, 1994; see also Fincham, 1990).

When the recombination occurs just subsequent to the early divisions of the dikaryon, the result is a comparatively "lightly" RIP mutated gene sequence, with few or no mutations affecting the expression of the gene product. More extensive mutation apparently destroys the homology necessary for the recombination to occur, preventing looping out of the intervening sequences (Cambareri, et al., 1991). Thus by genetically selecting for the "loop out" type of progeny, the highly mutagenic RIP process can be attenuated, and a large population of lightly altered gene sequences can be quickly and easily obtained.

In addition, the intrachromatid recombination event that reduces the copy number, and thus attenuates RIP, also serves to diversify the population. The recombination can occur within any sequence shared between the two duplicated gene sequences, each of which may carry different mutations, so that each pair of mutated gene sequences can give rise to a large number of variants in a single sexual cycle. Each recombination event will therefore add to the diversity of the population, since new combinations of sequence will result at each selected event. The result of this additional step will be to dramatically amplify the variability in the diversified population. A schematic representation of this diversification process is illustrated in FIG. 2.

Other methods of the present invention include use of unlinked duplications of the target gene sequence. "Linked" and "unlinked" refer to both physical linkage, such as the occurrence of sequences on the same or separate polynucleotides (i.e. chromosomes), and/or genetic linkage, such as where two sequences behave as unlinked even though they are physically linked. Unlinked gene sequences are not RIP mutated as efficiently as linked duplications. The frequency of progeny affected ranges anywhere from 10 to 80%, and the number of mutations induced in the target gene is also lower. The length of the duplication also affects the efficiency of RIP mutation. The observed minimum sequence length for efficient induction of RIP mutation is about 300 basepairs (bp) in linked duplications and about 500 bp in unlinked duplications. The relative severity of RIP mutation can also be controlled by altering the incubation temperature during the cross, or by age selection of the sexual progeny isolated (Cambareri, unpublished observations, (Singer, Kuzminova, Tharp, Margolin, & Selker, 1995a).

By use of these alternatives, the present invention permits the 'tuning' of the diversification process. For example, a single copy of an expression construct containing a cDNA for a human immunoglobulin kappa light chain under the control of a fungal promoter can be transformed into *N. crassa* at a particular locus like the his-3 gene. Instead of inserting an additional copy of the entire kappa cDNA, only the variable region of the kappa chain (Vk) is duplicated by transformation at another marked locus, such as the am gene. When crossed, the duplicated Vk sequence will trigger RIP mutations to occur only within the variable region of the duplicated kappa genes, leaving the constant region of the complete expressed gene intact. Progeny that have the altered expression locus (His-3 plus), but not the triggering duplication (Am minus) under the attenuating conditions outlined above, are then selected. These progeny can then be screened for altered binding properties by fusing the cells to an immunoglobulin gamma chain-expressing strain to create a panel of heterokaryons expressing the library of diversified kappa light chain genes and the resulting immunoglobulin product. The expression of such heterologous dimeric proteins in fungi is disclosed in U.S. Pat. No. 5,643,745, which is hereby incorporated by reference.

In addition, the methods of the present invention utilizing the diversification properties of RIP mutation with or without associated recombination can be combined with other gene shuffling technology, such as that disclosed in U.S. patent application Ser. No. 08/977,171 (Reagents and Methods for Diversification of DNA, filed Nov., 1997), resulting in further increases in variability within target sequences in the pool of isolates. The gene shuffling technology of that patent application utilizes a recombination "hot spot" at a locus called cog. Similar to the premeiotic RIP mutation mechanism, meiotic recombination at the cog locus is activated during a sexual cross. When crossed, *Neurospora* strains with the rec-2 genotype may engage in meiotic recombination at the cog locus in 30% of all selected progeny (Yeadon & Catcheside, 1998). Gene conversion tracts (sequence information transferred from one gene copy to the other) that range from greater than 5900 bp to 31 bp (and may be as small as single basepair changes) have been identified. More detailed analysis of progeny with a recombination event near cog revealed the occurrence of 11 independent recombination events within this locus in a single cell.

The combination of the present invention with the methods of U.S. patent application Ser. No. 08/977,171 creates multiple options for generating molecular diversity. One option entails use of the present invention (linked duplication RIP mutation and premeiotic recombination, or unlinked duplication RIP mutation attenuated by selection for progeny age or cross temperature), as separate, stand alone diversification technologies (see example in FIG. 2).

A second option combines either of the two diversification technologies by inserting a tandem repeat of a target sequence to be diversified at the cog locus while placing a single copy of the target sequence or homologue thereof at the cog locus of the opposite mating type strain. When crossed the parent with the duplicated target sequence will have undergone premeiotic mutation and recombination. Subsequently, and during meiosis, recombination at cog shuffles the gene sequence having undergone RIP mutation and looping out, together with the non-mutated target sequence from the other parent of the cross. This essentially results in a 'backcross' of the RIP mutated sequence to the non-mutated sequence, which improves the likelihood of recovering active, but altered target sequences. A further variation of this combination would be to use unlinked RIP mutation as described above, with one of the unlinked duplications at the his-3, cog locus, followed by homologous meiotic recombination driven by cog with a non-mutated gene sequence from the other parent. This option also permits non-'backcross' diversification when a single copy of a homologue of the target sequence is used at the cog locus of the opposite mating type strain.

In a third option, both strains contain tandem duplications of a gene sequence at the cog locus. Under these conditions, the present invention would alter and resolve the tandem duplications during premeiotic mutation and recombination. This would be followed by further shuffling during meiosis, resulting in the largest possible pool of altered genes. Variations would include unlinked sequence duplications in one or both parents (see example in FIG. 3).

As will be clear to one skilled in the art, any of the above options can be applied toward the expression of gene products for subsequent formation of heterodimeric proteins as discussed above.

The present invention provides methods and compositions for directed evolution of nucleic acids by in vivo diversification of polynucleotide sequences. Target sequences for directed evolution are transformed into cells capable of premeiotic mutation and recombination and/or meiotic recombination. To generate diversity in the target polynucleotide sequence, two (or more) identical copies of the target sequence are introduced into cells that subsequently can undergo mutation within a specialized dikaryotic cell during the premeiotic stage of its lifecycle.

After introduction into the fungal cell, the duplicated sequences are mutated by the RIP mutation phenomenon and/or premeiotic recombination upon induction of the sexual cycle. During the possible intrachromatid recombination events, one (or more) of the duplicated copies may be lost. In another embodiment of the invention, the diversified target sequence(s) may be further subjected to meiotic recombination after a sexual cross with another cell as described above.

Polynucleotide sequences suitable for in vivo diversification by the present invention may be from any source, including any eukaryote, prokaryote, virus or bacteriophage of interest, whether previously known or unknown. The sequences may also be previously characterized or uncharacterized. Artificial or synthetic sequences, whether previously subjected to alterations such as modification and mutagenesis or not, may also be diversified by use of the present invention. In a preferred embodiment, the polynucleotide sequences are in the form of DNA. In another preferred embodiment, the DNA is double stranded. The polynucleotide sequences may be of any functionality, including those that encode for proteins (such as enzymes, structural or regulatory proteins, and transporters) or nucleic acid products (such as functionally active ribozymes, regulatory or structural RNAs) and those that serve a structural role as DNA or RNA. Also included within the range of polynucleotide sequences are those that encode one subunit in a dimeric or multimeric protein.

In preferred embodiments of the invention, the target sequence is operably linked to sequences that regulate its expression. The one or more duplications of the target sequence, however, need not be similarly situated. As such, any expression of the target sequence, whether before or after diversification, will involve the expression of only one copy of the target sequence.

Alternatively, the target polynucleotide sequences may be regulatory sequences capable of controlling expression of other sequences. In a preferred embodiment, such regulatory sequences may be placed in a context with sequences encoding a reporter gene with duplication of the target regulatory sequences elsewhere in the cellular genome. Diversification of such sequences may result in increased or decreased levels of expression from the regulatory sequences as well as altered regulation of such sequences, all of which may be readily detected based on expression of the reporter gene.

To manipulate nucleic acids as described above, the practice of the invention employs, unless otherwise indicated, molecular biology, microbiology, and recombinant DNA techniques that are well within the skill of the art. Such techniques are explained fully in the literature. See for example, e.g., Maniatis et al., *Molecular Cloning: A Laboratory Manual* (1982); D. N. Gover et al. *DNA Cloning: A Practical Approach* (1985) Volumes I and II; *Oligonucleotide Synthesis* (M. J. Gait ed. 1984); *Nuclei Acid Hybridization* (Hames et al. eds. 1985); *Transcription and Translation* (Hames et al. eds. 1984); *Animal Cell Culture* (R. I. Freshney ed. 1986); *Immobilized Cells and Enzymes* (IRL Press 1986); B. Perbal, *A Practical Guide to Molecular Cloning* (1984).

In vivo diversification is generally limited to the duplicated sequences. As such, for diversification of the entire length of a target sequence, the entire length is duplicated at least once in the cell. Alternatively, the target sequence may be a portion of a larger sequence introduced into the cell, while the one (or more) duplications of the target sequence may be limited to just the portion in which diversification is desired. As explained above, the degree and extent of diversification may be "tuned" by controlling the duplicated sequences as well as the length of the duplication, selection for early recombination events (early recombinants), placement of the duplicated sequence(s) based on proximity or linkage, and altering the temperature of the cross, and/or age of the isolated progeny. In a preferred embodiment for the diversification of a protein encoding sequence, the target sequence is operably linked to regulatory elements capable of directing its expression while the one or more duplications of the target sequences, which may be restricted to portions of the target sequence in which diversification is desired, are not so operably linked.

Preferred cells for the practice of the invention include those of filamentous fungi, which refers to those fungi that can form a mycelium through a mass of branching, interlocking filaments and, although interrupted by cross walls, permit the passage of cytoplasm between compartments due to perforations in the cross walls. Filamentous fungi suitable for use in the invention include *Phycomycetes, Ascomycetes*, and *Basidiomycetes*.

*Ascomycetes* are distinguished from other fungi by the ascus, a saclike structure containing sexual spores, known as ascospores. The ascospores are the end product of mating, the fusion of male and female nuclei, two meiotic divisions, and usually one final mitotic division. *Basidiomycetes* are distinguished by sexual spores that form on the surface of a specialized structure.

The preferred filamentous fungus for use with the invention is of the group *Ascomycetes*, more preferably, from the genera *Neurospora, Penicillium, Fusarium, Gelasinospora, Ascobolus, Podospora*, and *Magnaporthe*. Examples of *Neurospora* species include *N. intermedia, N. crassa, N. sitophila*, and *N. tetrasperma*. Any species from other related genera that have premeiotic mutational processes analogous to RIP may also be used in the invention.

A target polynucleotide sequence is introduced into a haploid filamentous fungus, such as *Neurospora*, either by genetic or molecular means to create one or more duplicates of the sequence for in vivo diversification via RIP mutation. Genetic means for creating partial diploids are well described (Perkins, 1997). In embodiments using *Neurospora*, molecular transformation with exogenous DNA is a routine procedure most commonly accomplished by two methods. The first is through enzymatic digestion of the *Neurospora* cell wall, creating a spheroplast. The spheroplast is made transformation competent by treatment with $CaCl_2$ and the condensing agent PEG 4000 (Akins, 1985). Alternatively, transformation can be achieved by electroporation of conidia (Vann, 1995).

In practice of the invention, the duplicated sequence(s) can be inserted unlinked at ectopic loci or be targeted to specific loci. Targeted homologous integration is a rare event in *Neurospora*. Efficiencies can be increased significantly by increasing the length of homologous sequence in the transforming nucleic acid used (Asch & Kinsey, 1990). In addition, methods for selection of homologous integration at specific loci in *Neurospora crassa* are known in the art. Plasmid vectors and strains exist for the insertion of DNA into the his-3 locus (Aramayo & Metzenberg, 1996; Sachs & Ebbole, 1990) and the am locus (Cambareri & Kinsey, 1994) of *Neurospora*.

One factor to be addressed by the present invention in using RIP mutations for in vivo diversification of polynucleotide sequences is the methylation of cytosines at the 5 position. This is frequently associated with RIP mutation in cases where large numbers of transition mutations are induced in the target DNA. Lightly RIP mutated sequences, however, are rarely subject to methylation (Singer, Marcotte, & Selker, 1995b). In cases where large numbers of transitions are induced, methylation is maintained by the cell maintenance methylases. To avoid or minimize the presence of such methylated cytosines, the methylation process is reversible by 1) the addition of the cytosine analog, 5-Azacytidine; 2) by mutation of the dim-2 gene (Defective In DNA Methylation); or 3) use of an eth-1 strain (ethionine resistance) which is defective in S-adenosyl methionine (SAM) transferase (Foss, Roberts, Claeys, & Selker, 1993).

The substitution mutations induced by the in vivo diversification methods of the invention are possible transitional mutations at every C or G nucleotide in the duplicated sequence(s). This results from premeiotic RIP mutations being of a specific type: G to A and C to T transitions. While all C and G nucleotides in the duplicated sequence(s) are thus susceptible, there exists a dinucleotide nearest neighbor bias, with the 5' Cs of CpA>CpG=CpT>CpC in descending frequency of mutation (Cambareri, et al., 1989). A compilation of sequence data from RIP mutated DNA shows the C:G pair of CpA to be altered 64% of the time whereas CpC dinucleotides are altered only at a frequency of 5% (Irelan & Selker, 1996).

In application of the invention to cases of target sequences that encode a polypeptide product, the resulting changes in the encoded polypeptide due to RIP mutations are of interest. Many RIP mutation-induced changes are silent, and even more result in conservative amino-acid substitutions. Table 1 shows the potential pathways available for RIP diversification. It is noted that very few primary RIP mutations result in stop codons. 81 changes can be produced in the 47 C or G-containing codons when a single C or G is subject to RIP mutation (referred to as 1° RIP products) and only 3 of these result in stop signals (all three are in dinucleotide contexts giving less frequent mutation). The 64 codons still available for further change to 2° RIP products (i.e. still with Cs or Gs) can be further diversified to 84 new codons, only 4 of which result in translational stops. As such, use of the present invention can produce diversified sequences comprising silent, conservative, and/or non-conservative mutations depending on the codons present in the target sequence.

TABLE 1

Pathways of RIP diversification.

| AMINO ACID | CODON | 1° RIP PRODUCT | 2° RIP PRODUCT | 3° RIP PRODUCT |
|---|---|---|---|---|
| Alanine (A) | GCC | GTC(V) | ATC(I) | ATT(I) |
| | | | GTA(V) | ATT(I) |
| | | GCT(A) | GTT(V) | ATT(I) |
| | | | ACT(I) | ATT(I) |
| | | ACC(T) | ACT(T) | ATT(I) |
| | | | ATC(I) | ATT(I) |
| | GCG | GCA(V) | GTA(V) | ATA(I) |
| | | | ACA(T) | ATA(I) |
| | | GTG(V) | GTA(V) | ATA(I) |
| | | | ATG(M) | ATA(I) |
| | | ACG(T) | ACA(T) | ATA(I) |
| | | | ATG(M) | ATA(I) |
| | GCT | GTT(V) | ATT(I) | |
| | | ACT(T) | ATT(I) | |
| | GCA | GTA(V) | ATA(I) | |
| | | ACA(T) | ATA(I) | |
| Arginine (R) | AGA | AAA(K) | | |
| | AGG | AAG(K) | AAA(K) | |
| | | AGA(R) | AAA(K) | |
| | CGA | CAA(Q) | TAA(.) | |
| | | TGA(.) | | |
| | CGC | CGT(A) | CAT(H) | TAT(Y) |
| | | | TGT(C) | TAT(Y) |
| | | TGC(S) | TAC(Y) | TAT(Y) |
| | | | TGT(C) | TAT(Y) |
| | | CAC(H) | CAT(H) | TAT(Y) |
| | | | TAC(Y) | TAT(Y) |
| | CGG | CGA(A) | CAA(Q) | TAA(.) |
| | | | TGA(.) | |
| | | CAG(Q) | CAA(Q) | TAA(.) |
| | | | TAG(.) | |
| | | TGG(W) | TGA(.) | |
| | | | TAG(.) | |
| | CGT | CAT(H) | AAT(N) | |
| | | TGT(C) | TAT(Y) | |

TABLE 1-continued

Pathways of RIP diversification.

| AMINO ACID | CODON | 1° RIP PRODUCT | 2° RIP PRODUCT | 3° RIP PRODUCT |
|---|---|---|---|---|
| Asparagine (N) | AAC | AAT(N) | | |
| | AAT | | | |
| Aspartic acid (D) | GAC | GAT(D) | AAT(N) | |
| | GAT | AAT(N) | | |
| Cysteine (C) | TGC | TGT(C) | TAT(Y) | |
| | | TAC(Y) | TAT(Y) | |
| | TGT | TAT(Y) | | |
| Glutaminc acid (E) | GAA | AAA(K) | | |
| | GAG | GAA(E) | AAA(K) | |
| | | AAG(K) | AAA(K) | |
| Glycine (G) | GGG | GGA(G) | GAA(E) | AAA(K) |
| | | | AGA(R) | AAA(K) |
| | | AGG(K) | AGA(R) | AAA(K) |
| | | | AAG((K) | AAA(K) |
| | | GAG(E) | GAA(E) | AAA(K) |
| | | | AAG(K) | AAA(K) |
| | GGA | GAA(E) | AAA(K) | |
| | | AGA(R) | AAA(K) | |
| | GGC | GGT(G) | GAT(D) | AAT(N) |
| | | | AGT(S) | AAT(N) |
| | | GAC(D) | GAT(D) | AAT(N) |
| | | | AAC(N) | AAT(N) |
| | | AGC(S) | | |
| | GGT | GAT(D) | AAT(N) | |
| | | AGT(S) | AAT(N) | |
| Histindine (H) | CAC | CAT(H) | TAT(Y) | |
| | | TAC(Y) | TAT(Y) | |
| | CAT | TAT(Y) | | |
| Isoleucine (I) | ATC | ATT(I) | | |
| | ATT | | | |
| | ATA | | | |
| Lysine (K) | AAG | AAA(K) | | |
| | AAA | | | |
| Methionine (M) | ATG | ATA(I) | | |
| Phenylalanine (F) | TTC | TTT(F) | | |
| | TTT | | | |
| Proline (P) | CCC | CCT(P) | CCT(L) | TTT(F) |
| | | | TCT(S) | TTT(F) |
| | | CTC(L) | CTT(L) | TTT(F) |
| | | | TTC(F) | TTT(F) |
| | | TCC(S) | TCT(S) | TTT(F) |
| | | | TTC(F) | TTT(F) |
| | CCT | CTT(L) | TTT(F) | |
| | | TCT(S) | TTT(F) | |
| | CCG | CCA(P) | CTA(L) | TTA(L) |
| | | | TCA(S) | TTA(L) |
| | | CTG(L) | CTA(L) | TTA(L) |
| | | | TTG(L) | TTA(L) |
| | | TCG(S) | TCA(S) | TTA(L) |
| | | | TTG(L) | TTA(L) |
| | CCA | CTA(L) | TTA(L) | |
| | | TCA(S) | TTA(L) | |
| Serine (S) | AGC | AGT(S) | AAT(N) | |
| | | AAC(N) | AAT(N) | |
| | AGT | AAT(N) | | |
| | TCA | TTA(L) | | |
| | TCC | TCT(S) | TTT(F) | |
| | | TTC(F) | TTT(F) | |
| | TCG | TCA(S) | TTA(L) | |
| | | TGG(L) | TTA(L) | |
| | TCT | TTT(F) | | |
| Threonine (T) | ACG | ACA(T) | ATA(I) | |
| | | ATG(M) | ATA(I) | |
| | ACA | ATA(I) | | |
| | ACC | ACT(T) | ATT(I) | |
| | | ATC(I) | ATT(I) | |
| | ACT | ATT(I) | | |
| Tryptophan (W) | TGG | TGA(.) | | |
| | | TAG(.) | | |
| Tyrosine (Y) | TAC | TAT(Y) | | |
| | TAT | | | |
| Valine (V) | GTG | GTA(V) | ATA(I) | |
| | | ATG(M) | ATA(I) | |
| | GTA | ATA(I) | | |

TABLE 1-continued

Pathways of RIP diversification.

| AMINO ACID | CODON | 1° RIP PRODUCT | 2° RIP PRODUCT | 3° RIP PRODUCT |
|---|---|---|---|---|
| | GTC | GTT(V) | ATT(I) | |
| | | ATC(I) | ATT(I) | |
| | GTT | ATT(I) | | |

The modification of the codons in target sequence, by specific mutagenesis prior to duplication transformation into the host cells of the invention, may be used to direct the course of diversification toward silent, conservative, or non-conservative mutations. For example, the use of codons "AGA" or "AGG" for arginine will result in either a silent or conservative mutation to lysine upon diversification with the present invention (see Table 1). But the use of codons "CGC", "CGG", and "CGT" for arginine will result in non-conservative mutations.

As an additional form of this embodiment of the invention, the cells of the second parent need only contain one copy (each) of a sequence sufficiently similar to the target sequence after initial diversification to permit meiotic recombination to occur. Stated differently, the cells of the second parent need not contain only the target sequence as originally introduced into the first cell. The cells of the second parent may instead contain a sequence that differs from that of the original target sequence so long as the difference is not sufficient to prevent meiotic recombination.

Another embodiment of the invention relates to crosses with cells of the second parent containing two (or more) copies of the same target sequence (in or near the same recombination "hot spot") that have also undergone premeiotic mutation and/or recombination. The presence of diversified sequences in both parents of the sexual cross results in an even larger range of diversified sequences after meiotic recombination.

In both of the immediately preceding embodiments of the invention, the target sequence in cells of the first parent may be operably linked to sequences that regulate its expression. The one or more duplications of the target sequence in either the first or second parent cells, however, need not be similarly situated. As such, any expression of the target sequence, whether before or after diversification including meiotic recombination, will involve the expression of only one copy of the target sequence. Alternatively, the at least one copy of the target sequence in cells of the second parent may also be operably linked to regulatory sequences such that they can also be expressed, even after meiotic recombination (gene conversion) events.

Numerous studies characterizing of the sexual cycle of filamentous fungi have been reported in the literature. Fungi can occur in single mononucleated cells that yield filamentous multinuclear strands, yeast cells, fruiting bodies with diverse spores, and/or cells that are differentiated sexually. They can also exist in multinucleated forms. The principal element of the growing form of a fungus as a mold is the hypha, a branching tubular structure, about 2 μm-10 μm in diameter. Hyphae grow by elongation at their tips (apical growth) and by producing side branches.

The vegetative growth of filamentous fungi involves nuclear division with cell division (mitosis). This type of cell division consists of asexual reproduction, i.e., the formation of a new clone without the involvement of gametes and without nuclear fusion by way of conidia. For example, the species of Neurospora contain in their nuclei seven different chromosomes, each having a single copy, i.e. the vegetative organism is haploid. This haploid state is typically maintained during mycelial growth and during asexual reproduction through the formation of conidia.

Sexual reproduction can also occur when two haploid cells (hyphae or conidia) of different mating type fuse to form a dikaryotic cell containing two distinct nuclei. The two haploid nuclei thus coexist in the same cytoplasm and, for a time, divide more or less in synchrony. If a cell initiates ascospore formation, however, the two different haploid nuclei can actually fuse to form a diploid nucleus, which contains pairs of homologous chromosomes. This diploid cell then begins meiosis.

Neurospora crassa may be induced into developing female sexual structures when organic nitrogen is limiting. Hyphae begin to aggregate, forming protoperithecia. Emanating from the protoperithecia, are specialized hyphal structures called trichogynes. Macroconidia, microconidia and mycelia of the opposite mating type serve as the male parent and attract the trichogyne of the opposite mating type by secretion of a mating type specific pheromone (Bistis, 1981; Staben, 1996). Once an individual conidia or mycelia has been grasped by the trichogyne, fusion occurs between the tip of the trichogyne and the male cell. Nuclei from the male cell are then transported through the trichogyne to the ascogonium of the protoperithecia (see FIG. 1, panel A; and Raju, 1992).

In the ascogonium, the ascogoneous hyphae become croziers. It is within the croziers where the parental cells of both mating types A and a undergo 8-10 rounds of cell division (see FIG. 1, panel B; and Fincham, Day, & Radford, 1979). At this point, roughly 24 hrs from addition of male cells to the protoperithecia, the now developing perithecia begin to swell and pigments are deposited coloring the perithecia black. Karyogamy occurs in the ascus (the only diploid stage of the entire life cycle) and is immediately followed by two meiotic and one mitotic event yielding 8 ascospores (see FIG. 1, panel C). The basal and lateral cells surrounding the binucleate cell can fuse and divide to create new crozier cells allowing for several asci to be produced from a the initial dikaryotic cell (Coppin, Debuchy, Arnaise, & Picard, 1997).

Immature ascospores can be seen by day 5. The ascospores continue to develop for another 5-7 days then they are released from the perithecia Raju, 1992). Prior to ascospore release, the ascus swells and the turgor pressure within increases. It is believed the increase in hydrostatic pressure causes an abrupt rupture of the asci, propelling the ascospores release (Read & Beckett, 1996).

The products of polynucleotide sequences that have undergone diversification using the present invention may be directly selected and/or screened for by analyzing the fungal progeny. By diversifying genes directly within a fungal host cell expression system, for example as disclosed in U.S. Pat. No. 5,776,730, many subsequent steps are saved. However, not all potential products can be produced and directly (or indirectly) assayed within the cells or in the extracellular medium. As such, the use of alternative methods of selection and/or screening pools of diversified sequences is within the scope of the invention. These methods include the rescue of sequences from ascospore progeny by PCR, or by traditional cloning techniques, followed by inserted into the expression system of choice and subsequent expression and detection or analysis. Altered products encoded by the diversified sequences can then be assayed in a more optimized system, and new variants identified for use or further diversification.

Additional methods for direct screening of the cells of the invention include use of a reporter construct, substrate or marker sensitive to the expression of a gene product or to the production of a particular metabolite or catabolic activity; detection of desirable catabolic activities; and determination of growth rates. The cells can also be screened and/or selected for altered viability under various growth and environmental conditions, such as but not limited to temperature, nutrient source, pH, humidity, oxygen concentration, light, physical (such as UV) or chemical mutagens, toxic agents, and osmolarity/salinity, conferred by expression or presence of the diversified sequences. Direct detection of gene products of interest, such as proteins, may be by the use of antibodies which recognize the protein of interest. Any method of antibody mediated protein detection known in the art may be practiced as a selection/screening step in combination with the diversification methods of the invention.

Alternatively, the presence of desirable diversified sequences may be assayed by detection of metabolites resulting from their expression. One such assay method is by use of commercially available microtiter plates which are sterile and contain filters of known sizes in the bottom of each well (e.g. 0.6 micron or 0.45 micron pore sizes) and which, when placed on a commercially available vacuum filter holder will deposit liquid media through the filter, into a second identically configured microtiter plate, keeping the media in the same order as the cells and the culture plate all the while maintaining the sterility of the original cell or heterokaryon culture in the original culture plate. The collected media can be tested for the presence of a desirable metabolite, increased or decreased metabolic activity, binding, toxicity or any other characteristic which can be measured. During this testing activity, the original fungal cell cultures can be stored at 4° C. or, if the testing is expected to require more than a week, the culture plate can be stored frozen with or without a cryopreservative added.

Upon identification of a culture that is producing a desirable metabolite, the cells can be removed from the culture plate and cultured on solid medium and after sufficient growth used to inoculate an expanded liquid culture. When grown under whatever the optimal conditions are for the particular fungal host used, this expanded host culture will produce the desired metabolite in sufficient quantities for further research evaluation or use.

If the metabolite is not secreted, a portion of the cell mass of each cell can be removed, disrupted by standard methods and the cell supernatant and debris assayed for the desirable metabolite. Once the cell that produces the desired metabolite has been identified, another portion of the cell mass can be used to make an expanded culture. Again, when grown under optimal conditions for the particular cell or heterokaryon, this expanded host culture will produce the desired product in sufficient quantities for further evaluation and use.

The present invention also encompasses the isolation of diversified sequences for subsequent use in numerous contexts. Diversified sequences encoding or constituting a desirable activity can be isolated, after detection of said activity, according to standard techniques known in the art. These isolated sequences may then be further diversified or recombinantly used in other cells or organisms for the expression of said activity.

Furthermore, the invention provides a means of studying the structure to function relationship of a target polynucleotide sequence by observing the sequence positions that are diversified, as well as the nature of the diversification. An art accepted means of studying structure/function is by generation of altered sequences followed by comparisons of changes in structure to changes in activity. The present invention provides a very effect means for the generation of altered sequences for such studies. By comparing a given target sequence before and after diversification in combination with the various gains or losses in functionality, information on the relationship between various structures encoded by the sequence and the functionality imparted thereby can be elucidated. Based on such information, additional polynucleotide sequences can be designed with alterations or combinations of alterations not found after in vivo diversification.

The present invention further provides kits containing one or more containers that contain cells of the present invention. As used herein, a container refers to a physical device into which cells can be placed and stored.

The following are definitions of terms as used in relation to the invention disclosed herein:

"Diversify" or "diversification" relates to the introduction of one or more alterations into a polynucleotide sequence or nucleic acid as well as any possible gene product encoded thereby. The preferred means of diversification in the present invention is by premeiotic mutation and/or recombination, and optionally meiotic recombination.

A "target polynucleotide sequence" or "target sequence" relates to any nucleic acid sequence of interest introduced into a host cell to be diversified. The target sequence may, for example, encode a protein of interest, but diversification may be directed to a portion of said sequence, such as a region containing the 3' end of the sequence. This is readily accomplished by limiting the duplication in the host cell to said region.

A "cross" relates to the duplication mediated diversification of the present invention wherein one polynucleotide sequence is "crossed" with one or more duplications of the sequence during premeiotic mutation and/or recombination. A "cross" may also refer to a "sexual cross" between two fungal cells of opposite mating types to permit meiotic recombination as part of the present invention.

A "metabolite" relates to any molecule resulting from a metabolic pathway, an intermediate reaction in a pathway, or as a by-product of such a pathway. It may be the product of a single gene product or biochemical reaction, or of a plurality of gene products and biochemical reactions.

A "gene product" relates to any functional molecule resulting from the expression of a polynucleotide sequence or nucleic acid.

A nucleotide sequence is "operably linked to" regulatory elements when the latter effect the expression of the former in a host cell.

An "expression unit" relates to a nucleic acid molecule that is operably linked to regulatory elements that direct the expression of the operably linked nucleic acid in a host organism under appropriate conditions. The regulatory elements of an expression unit may be those normally found with the nucleic acid or those recombinantly introduced.

"Transformation" or "transformed" relates to the introduction of exogenous nucleic acids into a cell when such exogenous nucleic acids have been introduced across the cell's membrane. For prokaryotes such as bacteria the exogenous DNA may be maintained on an episomal element such as a plasmid. Because filamentous fungi do have nuclei (are eukaryotic), most stably transformed fungus host cells contain the exogenous DNA integrated into a chromosome (although episomal forms of exogenous nucleic acids are possible), so that it is inherited by daughter cells through chromosomal replication.

A "host cell" relates to cells that have been, are or will be transformed with nucleic acids prepared by recombinant techniques, and includes the cell originally transformed and cultures and progeny thereof.

The following examples are intended to illustrate but not to limit the invention.

Construction of Expression Units Containing Polynucleotide Sequences

The expression units containing a target polynucleotide sequence are constructed using techniques well known in the art. In general, an expression unit is generated by placing a nucleic acid sequence into operable linkage with control sequences that direct the expression of the nucleic acid in the ultimate filamentous fungal host cell.

A variety of control elements are presently known in the art for directing the expression of an operably linked nucleic acid sequence in either a constitutive or inducible fashion. The choice of a control sequence will be based on the fungal strain used, conditions employed for culturing the fungus, the level of expression desired, and the nature of expression required (for example, inducible versus constitutive). A skilled artisan can readily utilize art-known control sequences for generating the expression units used in the present fungal host cells.

In addition to sequences that direct the transcription and translation of protein-encoding sequences, the expression units of the present in sequences, expression control elements that direct the export of a protein outside the cell. A review of secretory signals that are known in filamentous fungus are provided by Dalbey R. E., et al., *TIBS* 17:474-478 (1992). The skilled artisan can readily generate expression units that contain secretory signals without undue experimentation.

In the introduction of target sequences into cells, recombination units may be generated. In such cases, a polynucleotide sequence, optionally with operably linked regulatory sequences, is flanked by regions of DNA that contain sequences that are homologous to an integration site in the host fungal strain. The homologous sequences are then used to stimulate and direct homologous recombination between the recombination units and the host chromosome. The homologous sequences may be those capable of resulting in recombination with selectable markers as well as recombination "hot spots" in the host fungal strain. Intermediate hosts are sometimes used to produce intermediate vectors capable of transforming the ultimate fungal cells. The intermediate bacterial transformants can then be grown to obtain the desired quantities of DNA, which can be used to transform a desired filamentous fungus host. Examples of commonly available bacterial vectors that can serve as intermediate vectors include, for example, pBR322, pUC8 and pUC9.

General Procedure for Transformation of *N. crassa*

As explained above, polynucleotide sequences are used to transform parent host strains of a filamentous fungus. Strains of *Neurospora crassa* are publicly available from the Fungal Genetics Stock Center, but independently prepared strains can also be used. Mutant strains may be isolated de novo, as illustrated by Stadler et al. *Genetics* (1966) 54:677-685 and Haas et al. *Genetics* (1952) 37:217-26. Useful strains can also be obtained from D. D. Perkins from Stanford University. Strains are typically grown on 1× Vogel's Minimal Medium ("N medium") in cotton-plugged test tubes, with appropriate supplements being added depending on the strain's phenotype.

Spheroplasts are used as subjects for transformation. To form conidial spheroplasts, the fungus is inoculated onto 25 ml of solid N medium, with appropriate supplements in four to five 125-ml Erlenmeyer flasks, which have been plugged with cotton. The cultures are grown at room temperature for 5-7 days.

The conidia are harvested by adding 10 ml of N medium to each flask, replacing the cotton plug, and swirling the flask. The solids are allowed to settle for a few minutes. The conidial mixture is poured to an autoclaved cheesecloth bag hanging in the mouth of an Erlenmeyer flask and secured with one or more rubber bands. The filtrate is recovered, and the concentration of conidia is determined by a hemocytometer count, with chains being counted as one.

A volume of $2 \times 10^9$ conidia is added to 150 ml of liquid N medium containing 1.5% sucrose and appropriate supplements. The conidia are germinated in the cotton-plugged flask while shaking (150-200 rpm) for 5-6 hours at room temperature until more than 75% have germinated and the germ tubes are 1-4 conidial diameters in length. The cells are harvested by centrifuging at about 1500-2000 rpm for 10 minutes. The cell pellet is rinsed three times with water.

The pellet is then re-suspended in 10 ml of 1.0 M sorbitol, and the spheroplasts are prepared by enzymatic removal of the tough conidial cell wall with an enzyme under isotonic conditions, to prevent the "bursting" of the spheroplasts as they are formed. The protocol is adapted from the method of Vollmer and Yanofsky, *Proc Natl Acad Sci USA* (1986) 83:4869-73.

Specifically, in a sterile 250 ml Erlenmeyer flask, the conidial suspension is generally added to 50 mg of a solid enzyme sold by Novo Laboratories under the trade name Novozyrn 234. The mixture is shaken (100 rpm) at 30° C. for about an hour (±10 minutes) to digest the cell wall. The spheroplast formation process is monitored by examining a small aliquot of the mixture microscopically under a cover slip. Spheroplasts can be detected because they lyse osmotically when water is applied to one end of the cover slip. The process should be monitored frequently at the later stages of spheroplast formation.

The spheroplast mixture is decanted into a sterile 15-ml conical centrifuge tube, and the spheroplasts are recovered by centrifuging at 500 rpm (10 minutes) in a swinging bucket table top centrifuge. The resulting pellet is rinsed twice with 10 ml of 1.0 M sorbitol and then once with the following STC solution: 91 g sorbitol; 50 mM Tris-HCl; 50 mM $CaCl_2$; sufficient NaOH to adjust the pH to 8.0; and q.s. to 500 ml.

The final spheroplast pellet is suspended in a mixture of 16.0 ml STC, 200 UlDMSO, and 4 ml of the following PTC solution: 200 g polyethylene glycol sold under the trade name "4000" by Sigma; 50 mM Tris-HCl; 50 mM $CaCl_2$; sufficient NaOH to adjust the pH to 8.0; and q.s. to 50 ml.

The resulting suspension of spheroplasts can either be used directly or stored frozen in 1.0 ml aliquots at −80° C.

In a sterile, 15-ml screw-cap tube, 2.0 μl of 50 mM Spermidine solution, 5.0 μl of the plasmid DNA to be transfected, such as that containing the heterologous nucleic acid along with a selectable marker such as an altered beta-tubulin gene conferring benomyl resistance (usually at a concentration of about 1.0 mg/ml) and 5.0 μl of a 5 mg/ml heparin solution are mixed by flicking the tube. The spermidine solution is prepared by dissolving 12.73 mg of spermidine in 1.0 ml TE and adjusting the pH to 8.0, and can be stored at −20° C. The heparin solution is prepared by dissolving 50 mg of the sodium salt of heparin in 10 ml of STC and can be stored in frozen aliquots.

The contents of the tube are briefly spun (pulsed) in a tabletop centrifuge and then placed in an ice bath. About 50-100 µl of thawed spheroplasts are added to the tube. The mixture is then incubated on ice about 30 minutes, but incubation periods of about 20 minutes on ice have been successful. About 1 ml of PTC is added and mixed well by flicking the tube. The mixture is incubated further at room temperature for about 20 minutes.

A regeneration "Top" Agar is prepared by mixing: 20 ml 50× Vogel's Minimal Medium; 825 ml of water; 182 g sorbitol; and 28 g agar. The top agar is autoclaved and 100 ml of a 10× FIGS solution (containing 5 g/l fructose, 2 g/l inositol, 2 g/l glucose, and 200 sorbose) is added. 15 ml of the top agar is incubated at 50-55° C. and poured into the tube containing the spheroplasts and plasmid DNA. The contents are quickly mixed by flicking and inverting the tube 2-3 times and then uniformly poured onto a layer of plating "bottom" agar.

The "bottom" agar is prepared by mixing any required supplements, in 1× N medium; autoclaving; and adding 10× FIGS and benomyl (if benomyl resistance is used as a marker) to final concentrations of 1× and 0.5 µg/ml respectively. A volume of 25 ml of "bottom" agar is poured into a petri plate and allowed to harden.

After the top agar has been poured over the bottom agar, bubbles are removed by flaming. The plates are kept in an upright position until the top agar has solidified (about 5 minutes). If the top agar tends to harden prematurely, the bottom agar plates can be prewarmed. Once the top agar has solidified, the plates are incubated in an inverted position at 30° C.

For selection of the *N. crassa* transformants, the host is thus cultured on the appropriate medium (having composition only the transformed cells can utilize or containing an antibiotic to which only transformed cells are resistant) and incubated at about 34° C. An indication of a successful transformation can be seen about 24-36 hours after plating. Stable transformants are generally scored after three days of growth. The incubation period to detect transformants will vary depending on the host strain and the phenotypic marker.

Selected transformants can be screened for, expression of the target polynucleotide sequence by standard methods, such as PCR, an appropriate ELISA, Southern hybridization, and the like.

Alternatively, electroporation procedures can be used to transform freshly harvested conidia of filamentous fungus such as *Neurospora crassa* (Van, D. C. *Fungal Genetics Newsletter No. 42A (Supplement)* (1995)). In general, conidia are harvested from 7-28 day old cultures. The cells are washed in 1 M sorbitol solution and suspended at a final concentration of $2.5 \times 10^9$ cells/ml. Approximately 5 µg of linearized DNA is added to an aliquot of the conidial suspension and a portion of this is placed in the bottom of an electroporation cuvette, for example an electroporation cuvette with a 0.2 cm gap. An electroporator, such as an InVitrogen Electroporator II, is set with a voltage gradient of about 7.25 kV/cm and a setting of about 71 µF and about 200 ohms. Following electroporation, the cells are plated on appropriate media with or without a top agar essentially as described above.

Following transformation, a stable parental strain containing the heterologous nucleic acids may be established by expanding the culture on selective media for the particular host cell used with each parental strain.

References:

Akins, A. A. a. A. M. L. (1985). General Method for Cloning *Neurospora crassa* Nuclear Genes by Complementation of Mutants. *Molecular and Cellular Biology*(September), 2272-2278.

Aramayo, R., & Metzenberg, R. L. (1996). Gene replacements at the his-3 locus of *Neurospora crassa*. *Fungal Genet. Newsl.,* 43, 9-13.

Asch, D. K., & Kinsey, J. A. (1990). Relationship of vector insert size to homologous integration during transformation of *Neurospora crassa* with the cloned am (GDH) gene. *Molecular General Genetics,* 221, 37-43.

Barbato C, Calissano M, Pickford A, Romano N, Sandmann G, Macino G. (1996) *Mol Gen Genet,* 252(4):353-61.

Bistis, G. N. (1981). Chemotropic Interactions Between Trichogynes and Conidia of Opposite Mating-Type in *Neurospora crassa. Mycologia,* 73, 959-975.

Cadwell, C. R., & Joyce, G. F. (1993). Randomization of genes by PCR mutagenesis. *PCR Methods and Applications,* 2, 28-33.

Cambareri, E. B., Jensen, B. C., Schabtach, E., & Selker, E. U. (1989). Repeat-induced G-C to A-T mutations in *Neurospora. Science* 244(4912), 1571-5.

Cambareri, E. B., & Kinsey, J. A. (1994). A simple and efficient system for targeting DNA to the am locus of *Neurospora crassa. Gene* 142, 219-224.

Cambareri, E. B., Singer, M. J., & Selker, E. U. (1991). Recurrence of repeat-induced point mutation (RIP) in *Neurospora crassa. Genetics,* 127(4), 699-710.

Coppin, E., Debuchy, R., Amaise, S., & Picard, M. (1997). Mating Types and Sexual Development in Filamentous Ascomycetes. *Microbiology and Molecular Biology Reviews,* 61 (4), 411-428.

Crameri, A., Bermudez, E., Raillard, S., & Stemmer, W. P. C. (1998). DNA shuffling of a family of genes from diverse species accelerates directed evolution. *Nature,* 391, 288-291.

Fincham, J. R. S., Day, P. R., & Radford, A. (1979). *Fungal Genetics.* Oxford: Blackwell Scientific Publications.

Fincham, J. R. S. (1990) *Curr Genet,* 18: 441-45.

Foss, H. M., Roberts, C. J., Claeys, K. M., & Selker, E. U. (1993). Abnormal chromosome behavior in *Neurospora* mutants defective in DNA methylation. *Science* 262, 1737-1741.

Hamann A, Feller F, Osiewacz H D (2000) *Mol Gen Genet,* 263(6):1061-9.

Harris, S., Rudnicki, L. S., & Haber, J. E. (1993). Gene conversions and crossing over during homologous and homeologous ectopic recombination in *Saccharomyces cerevisiae. Genetics,* 135 (1), 5-16.

Irelan, J. T., Hagemann, A. T., & Selker, E. U. (1994). High frequency repeat-induced point mutation (RIP) is not associated with efficient recombination in *Neurospora. Genetics,* 138, 1093-1103.

Irelan, J. T., & Selker, E. U. (1996). Gene Silencing in filamentous fungi: RIP, MIP and quelling. *Journal of Genetics,* 75 (3), 313-324.

Perkins, D. D. (1997). Chromosome rearrangements in *Neurospora* and other filamentous fungi. *Advances in Genetics* 36, 239-398.

Raju, N. B. (1992). Genetic Control of the Sexual Cycle in *Neurospora. Mycological Research,* 96, 241-262.

Read, N. D., & Beckett, A. (1996). Ascus and Ascospore Morphogenesis. *Mycological Research: an international journal,* 100 (p11), 1281-1314.

Sachs, M. S., & Ebbole, D. (1990). The use of lacZ fusions in *Neurospora crassa. Fungal Genetics Newsletter,* 37, 35-36.

Selker, E., Cambareri, E., Garrett, P., Jensen, K., Haack, K., Foss, E., Turpen, C., Singer, M., & Kinsey, J. (1989). Use fo RIP to inactivate genes in *Neurospora crassa. Fungal Genetics Newsletter,* 36, 73-76.

Selker, E., Cambareri, E., Jensen, B., & Haack, K. (1987). Rearrangement of duplicated DNA in specialized cells of *Neurospora. Cell,* 51 741-752.

Singer, M., Kuzminova, E., Tharp, A., Margolin, B., & Selker, E. (1995a). Different frequencies of RIP among early vs. late ascospores of *Neurospora crassa. Fungal Genetics Newsletter,* 42, 74075.

Singer, M. J., Marcotte, B. A., & Selker, E. U. (1995b). DNA methylation associated with repeat-induced point mutation in *Neurospora crassa. Mol. Cell. Biol.,* 15, 5586-5597.

Staben, C. (1996). The Mating-type Locus of *Neurospora crassa. Journal of Genetics,* 75 (No. 3), 341-351.

Stemmer, W. P. C. (1994). DNA shuffling by random fragmentation and reassembly: In vitro recombination for molecular evolution. *PNAS USA,* 91, 10747-10751.

Suzuki, M., Baskin, D., Hood, L., & Loeb, L. A. (1996). Random mutagenesis of *Thermus aquaticus* DNA polymerase I: concordance of immutable sites in vivo with the crystal structure. *PNAS USA,* 93 (18), 9670-9675.

Vann, D. C. (1995). Electroporation-based transformation of freshly harvested conidia of *Neurospora crassa. Fungal Genet. Newsl.,* 42A, 53.

Yeadon, P. J., & Catcheside, D. E. (1998). Long, interrupted conversion tracts initiated by cog in *Neurospora crassa. Genetics,* 148(1), 113-22.

Zhang, J., Dawes, G., & Stemmer, W. P. C. (1997). Directed evolution of an effective fucosidase from a galactosidase by DNA shuffling and screening. *PNAS USA,* 94, 4504-4509.

All references cited herein are hereby incorporated by reference in their entireties, whether previously specifically incorporated or not. As used herein, the terms "a", "an", and "any" are each intended to include both the singular and plural forms.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

The invention claimed is:

1. A method for diversifying an initial target polynucleotide sequence comprising:
   introducing two or more copies of said initial sequence into a filamentous fungal cell wherein at least two identical copies are tandemly linked;
   generating a population of diversified sequences which are diversified relative to the initial target sequence by culturing the filamentous fungal cell under conditions that promote premeiotic mutation and/or recombination; and
   selecting said diversified sequence is functionally active, wherein the initial target polynucleotide sequence is exogenous to the filamentous fungal cell.

2. The method of claim 1 wherein said mutation is RIP mutation.

3. The method of claim 1 wherein said sequence encodes an active gene product, regulates the expression of other sequences, or serves a structural role.

4. The method of claim 1 wherein said cell is selected from the groups *Phycomycetes, Ascomycetes,* and *Basidiomycetes.*

5. The method of claim 4 wherein said cell is selected from the group consisting of *Neurospora, Penicillium, Fusarium, Gelasinospora, Ascobolus, Podospora,* and *Magnaporthe.*

6. The method of claim 5 wherein said cell is selected from the group consisting of *N. intermedia, N. crassa, N. sitophila,* and *N. etrasperma.*

* * * * *